United States Patent
Igler

(10) Patent No.: US 10,460,079 B2
(45) Date of Patent: Oct. 29, 2019

(54) METHOD AND MEDICAL APPARATUS FOR OPTIMIZATION OF THE PERFORMANCE OF A PROCEDURE INVOLVING MEDICAL IMAGING ON A PATIENT

(71) Applicant: Siemens Healthcare GmbH, Erlangen (DE)

(72) Inventor: Harald Igler, Hausen (DE)

(73) Assignee: Siemens Healthcare GmbH, Erlangen (DE)

( * ) Notice: Subject to any disclaimer, the term of this patent is extended or adjusted under 35 U.S.C. 154(b) by 27 days.

(21) Appl. No.: 15/712,891

(22) Filed: Sep. 22, 2017

(65) Prior Publication Data
US 2018/0089380 A1 Mar. 29, 2018

(30) Foreign Application Priority Data
Sep. 23, 2016 (DE) ......................... 10 2016 218 364

(51) Int. Cl.
| | |
|---|---|
| A61B 5/00 | (2006.01) |
| G06F 19/00 | (2018.01) |
| G06N 20/00 | (2019.01) |
| G16H 40/63 | (2018.01) |
| G16H 50/50 | (2018.01) |
| G06Q 50/22 | (2018.01) |
| G06T 1/00 | (2006.01) |
| A61K 35/60 | (2006.01) |

(52) U.S. Cl.
CPC ............ *G06F 19/34* (2013.01); *G06F 19/321* (2013.01); *G06N 20/00* (2019.01); *G06Q 50/22* (2013.01); *G06T 1/0007* (2013.01); *G16H 40/63* (2018.01); *G16H 50/50* (2018.01)

(58) Field of Classification Search
CPC ............ G06F 19/00; A61K 9/00; G06Q 50/00
USPC .................................. 382/128–134; 424/523
See application file for complete search history.

(56) References Cited

U.S. PATENT DOCUMENTS

2004/0122487 A1 * 6/2004 Hatlestad ............. A61B 5/0031
607/60

FOREIGN PATENT DOCUMENTS

DE 102012212265 A1 1/2014

OTHER PUBLICATIONS

Definition of Variance analysis / comparison of budgeted and actual figures CBA, IGC Controller Dictionary, International Group of Controlling (2010).
"Welcome to the Cognitive Era," IBM Outthink—Cognitive Business with Watson (2015).
Benson, "System measures ambulatory care quality" (Article Preview), Physician Executive (1990).
Hohl, "Big Data," SecuPedia, the platform for security information (2015).
Hug, "Wegweisende Modelle zur Weiterentwicklung der Pflege im Krankenhaus," Staedtisches Klinikum Karlsruhe gGmbH (2011).

* cited by examiner

*Primary Examiner* — Abolfazl Tabatabai
(74) *Attorney, Agent, or Firm* — Schiff Hardin LLP

(57) ABSTRACT

In the performance of a procedure on a patient by a medical system, target values for each substep of the procedure are determined in a computer. Actual values for each substep of the procedure are detected. The target values are compared in the computer to the actual values for each substep of the procedure, in order to determine a deviation between the target values and the actual values.

13 Claims, 3 Drawing Sheets

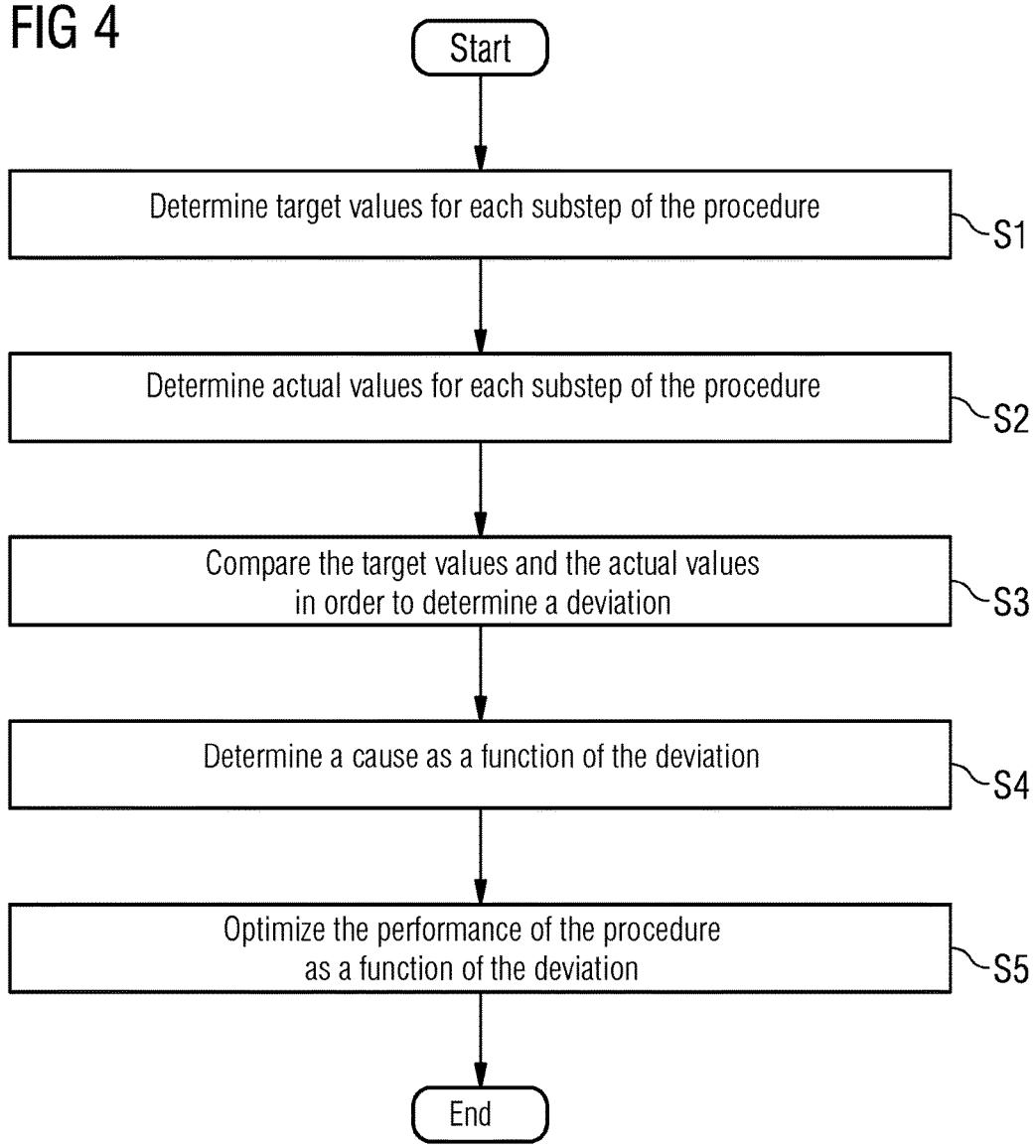

METHOD AND MEDICAL APPARATUS FOR OPTIMIZATION OF THE PERFORMANCE OF A PROCEDURE INVOLVING MEDICAL IMAGING ON A PATIENT

BACKGROUND OF THE INVENTION

Field of the Invention

The present invention optimizes the performance of procedures on a patient using a medical system (e.g. an X-ray system, an MR system, a CT system or combinations thereof), meaning that, for example, clinical processes during the examination or treatment of the patient can be automatically optimized.

Description of the Prior Art

Numerous different steps are frequently necessary when examining or treating patients. Different technical devices are increasingly being deployed to perform these steps and, for example, in the case of operations on the patient, the same technical device may be adapted or restructured. The workflow or performance of these steps for examining or treating the patient is hence precisely scheduled. If a problem occurs with any of these steps (e.g. of a technical or person-related nature), such as an unscheduled time delay, this generally results in subsequent scheduled patient examinations or patient treatments being delayed, or in extreme cases the delay can be life-threatening or at any rate very unpleasant for the patient currently being examined or treated.

SUMMARY OF THE INVENTION

An object of the present invention is to optimize the performance of a procedure on a patient by a medical system, in order to reduce the likelihood of the occurrence of the above-mentioned problems during the performance.

In the context of the present invention, a method for performing a procedure on a patient by a medical system is provided. This means that with the use of the medical system (for example a magnetic resonance (MR) system or a computed tomography (CT) system or a combination thereof) the procedure is performed on the patient (e.g. an examination or a treatment). The method includes the following steps.

Target values for each substep of the procedure are determined. The target values are a predefined time period in which the respective substep is to be performed, or a measure of quality which should comprise the result (e.g. the image data) of the substep. However, the target values can also be so-called patterns, i.e. analysis results, of which the substep is to consist.

Actual values for each substep of the procedure are detected. The actual values are e.g. time periods that are automatically determined for each substep, and that indicate how long the respective substep has actually lasted, or a measure of quality which includes the result of the substep. The actual values can also be the patterns of which the substep performed actually consists.

The target values are compared with the actual values for each substep of the procedure, in order to determine, independently of the comparison or the difference between the respective target value and the respective actual value, a deviation between the respective target value and the respective actual value for each substep. In the case of the patterns, a check is made as to whether the substep performed actually consists of the patterns prescribed by the target values. If the substep is aborted, the substep generally does not consist of all patterns prescribed by the target values, so that in this case a deviation is present.

If necessary, previously unscheduled repeat measurements also occur as a substep, since the scheduled measurement (i.e. the scheduled substep) supplied an unsatisfactory result. In this case a deviation is likewise present, in that the target value (e.g. a target time period) for the unscheduled substep contains e.g. the value 0.

The inventive determination of the deviation between the target values and the actual values is a necessary step in order to optimize the performance of the procedure. Based on the knowledge of the deviation for a particular substep, the substep can be optimized such that the substep no longer results in a deviation in future procedures. The optimization of the substep thus results in an optimization of the entire procedure.

According to a preferred inventive embodiment, the inventive method includes the following additional steps.

A comparison value is determined for each substep, by the difference being calculated between the target value corresponding to the substep and an actual value corresponding to the sub step.

The deviation is provided as an output only if the amount of the comparison value is higher than a predetermined threshold value. In this case the threshold value can be determined as a function of the respective substep, or as a function of whether the comparison value is positive or negative. The deviation can be provided as an output in the form of the comparison value, or only as information that a deviation is present.

According to this embodiment (positive and negative) deviations are provided as an output if the corresponding actual value differs in a relevant manner from the associated target value. The output can be presented to the person who is supervising or performing the procedure with the medical system, for example. As a result, it is possible for this person first to confirm the (in particular negative) deviation, or second to determine a possible cause of this deviation and to provide the cause to the optimization algorithm.

If a deviation occurs, a so-called analysis pattern can be generated, which includes numerous analysis results of the substep in which the deviation occurred. The analysis pattern can then be employed to (automatically) determine the cause or to determine the target values for future substeps (including in the case of other medical systems).

It is also possible for the inventive method to automatically determine the cause of the deviation between the target value and the actual value for a particular substep.

The inventive method can, for example, automatically determine the cause of the deviation on the basis of parameters of the respective substep. These parameters, which are provided to the inventive method by the user or are automatically captured by the inventive method, can include the following information:

The weight, age, capacity, physical and/or mental condition of the patient. For example, the preparation for an MR examination generally takes longer in the case of very old, large, anxious, frail and/or morbid patients. The capacity, physical and/or mental condition can in this case be estimated in each case automatically as a function of the patient using a corresponding key figure or by the person who is performing the procedure with the medical system.

The thermal load of the medical system during the performance of the substep and the current temperature of a coolant for the medical system. During the performance of multiple substeps with a high thermal load it can happen, as a function of the temperature of the coolant, that one of these substeps is delayed, in order to prevent an overload of the medical system.

The age of or damage to components of the medical system. A substep in which a heavy load is placed on the medical system can be automatically delayed by the medical system, in order to prevent the system being overloaded specifically in the case of old or damaged components.

The automatically determined cause can be displayed as information for the person who is performing the procedure by the medical system. The cause also can be stored e.g. in an archiving system together with further information on the respective substep (e.g. the target value and the actual value) in order to take account of the cause in future procedures containing the same substep (for example for user guidance).

According to a further embodiment, a procedure is performed by the medical system on multiple patients (i.e. the patients are each treated or examined in succession using the medical system). In this case a sequence in which the procedures are performed is fixed as a function of the previously determined cause, in order to reduce the deviations in the procedures.

For example, it is possible to detect that a subset of the procedures to be performed in each case includes a substep in which an excessively high thermal load of the medical system has been identified (e.g. as a function of the temperature of the coolant) as a cause of a negative deviation (i.e. actual value>target value in the case of times or actual value<target value in the case of measures of quality). In this case the sequence of the procedures can then be fixed such that procedures that do not belong to the subset are in each case performed between two procedures that do belong to said subset, such that as far as possible two procedures of said subset are never executed directly one after the other.

In addition, the cause can be provided as an output prior to the performance of a substep of another procedure. In this case, the substep of the other procedure corresponds to the substep for which the cause was determined based on the deviation between the target values and the actual values. Because the cause is provided as an output prior to the performance, the deviation should be prevented during the actual performance of the substep of the other procedure, for example in that the substep is performed more carefully (using appropriate user guidance).

For example, causes (e.g. possible errors) of a possible deviation can be output prior to the performance of a current substep together with likelihoods of occurrence for the respective cause. The causes can be determined automatically, for example, as the reason for a negative deviation during substeps that correspond to the substep currently to be performed. By the causes as an output to the person executing the current substep, that person is warned, meaning that the likelihood is increased that the current substep is being performed without a negative deviation.

The substeps can in each case be at least one of the following activities:

Registering a patient, wherein the most important data on the patient (e.g. height, age, weight) is recorded.

Preparing the next substep. Such preparation may comprise the preparation of the patient for the performance of the next substep and/or the preparation of the medical system for the performance of the next substep.

Evaluating the previous substep. In a similar manner as for the preparation, such evaluation can firstly comprise the evaluation of the patient and secondly the evaluation of the medical system.

A measurement, during which measurement results are captured, which the medical system captures from the patient. A measurement can also include multiple submeasurements, wherein each of said submeasurements can be regarded as a substep. Measurements include imaging methods, such as e.g. MR and/or CT methods. The measurement results can for example be X-ray data in the case of an X-ray device, image data in the case of an MR system, image data in the case of a CT system or ultrasound data in the case of an ultrasound device. Various measurement methods offered to the user exist for the measurements (in particular in the case of MR and/or CT measurements, sequences containing different parameters exist). The different measurement methods are available as a respective possible selection when scheduling the procedure.

An intervention or an operation on the patient by the medical system. In the substep, the patient is operated on, wherein generally a prior or subsequent substep comprises a measurement, as described above. In this case a wide variety of operation techniques can be employed.

Treatment or therapy for the patient with the aid of the medical system. In this substep the patient is for example irradiated by the medical system. Other therapies, such as e.g. interventional therapies, in particular heat treatment, are also conceivable.

According to a further embodiment, one of the target values for the respective substep can be a target time period. In this case a target time period determines a time period in which the respective substep is to be performed. In a similar manner, at least one of the actual values for the respective substep corresponds to an actual time period. The actual time period corresponds to a time period in which the respective substep was currently performed.

As noted above, the deviation between the target values and the actual values can be determined in this embodiment on the basis of the difference between the target time period and the actual time period.

According to a further embodiment, at least one of the target values or all target values of the respective substep can be determined using a simulation (i.e. automatically).

In this case the target values are determined automatically on the basis of a simulation on the basis of parameters or preconditions of the respective substep. Besides the parameters explained above to determine the cause of the deviation, the parameters or preconditions can also include the following information to determine the target values:

The type of measurement, treatment or intervention to be performed. Said information also contains the details of which component (e.g. MR system, CT system) of the medical system is employed to perform the substep.

At which point or on which organ of the patient the measurement, treatment or intervention to be performed is executed.

Which aids (such as e.g. head coil, infusion pump) of the medical system are necessary for the performance of the substep.

The simulation or determination of the target values of the respective substep can also take place as a function of the cause which has previously been determined in accordance with the invention as the cause of the deviation between the target values and the actual values of a substep comparable to the respective substep.

Because during the determination of the target values a previously determined cause is taken into account, the target values can advantageously be determined such that during the performance of the substep no deviation occurs. This is the case for positive and for negative deviations. This means that in the case of a negative deviation the target value is generally correspondingly enlarged (reduced), whereas in the case of a positive deviation it is correspondingly reduced (enlarged).

According to the invention, a positive deviation, in which e.g. the actual time period is smaller than the corresponding target time period, can be employed to optimize the performance of a procedure on a patient by the medical system.

Besides the previously described determination of the target values as a function of a positive deviation the positive deviation can be communicated together with the cause of the positive deviation, so that in future in the case of corresponding substeps said positive deviation, and thus an improvement in the entire procedure, occurs as frequently as possible.

In the context of the present invention, an apparatus for a medical system is also provided. The apparatus has a control computer and a sensor arrangement configured to perform a procedure on a patient by the medical system. The apparatus is configured in order to determine, with the use of the control computer, target values for each substep of the procedure, in order to detect actual values for each substep of the procedure with the sensor arrangement, and to compare the target values to the actual values for each substep of the procedure by the control computer, in order as a function thereof to determine a deviation between the target values and the actual values.

The advantages of the inventive apparatus correspond substantially to the advantages of the inventive method.

In addition, the present invention relates to a medical system that includes such an inventive apparatus.

The medical system can be at least one of the following:
a magnetic resonance system,
a computed tomography system,
an angiography device,
an X-ray device,
an ultrasound device.

The present invention also encompasses a non-transitory, computer-readable data storage medium encoded with programming instructions (program code) that, when the storage medium is loaded into a computer or computer system of a medical system, cause the computer or computer system to operate the medical system in order to implement any or all embodiments of the method according to the invention, as described above. The program code may be a source code (e.g. C++), which must still be compiled and linked or which only has to be interpreted, or an executable software code, which for execution purposes only has to be loaded into the corresponding computer.

The electronically readable data carrier can be, e.g. a DVD, a magnetic tape, a hard disk or a USB stick, on which electronically readable control information, in particular software (cf. above), is stored.

With the present invention, errors that occur during the performance of the procedure (i.e. in the workflow) can be immediately identified and hence suppressed very rapidly, in order to prevent the same errors in future. In the case of the ever more frequently occurring combination of multiple medical devices (e.g. in the case of neurological examinations using a magnetic resonance system or when employing surgery combination couches that can be employed for the operation and for the examination, e.g. in an MR system) this represents a major advantage. In this case, knowledge that has been determined inventively for a substep for one medical system can also be used for a substep for another medical system if the latter substep is similar to the first-mentioned substep. In other words a cause of the deviation between the target values and the actual values of the first-mentioned substep can also be employed as the cause of a possible deviation between the target values and the actual values in the case of the latter substep and for the better scheduling of said substep. This means the scheduling (e.g. the determination of the target values) of a substep for a CT system can be undertaken on the basis of causes that are determined for a substep for an MR system.

In addition, with the present invention a continuous workflow can be guaranteed when performing multiple procedures on patients by a medical system, so possible errors are identified and thereby prevented, as a result of which the process is continuously optimized.

According to the invention the medical system can be selected as a function of previously determined causes of the deviation between target values and actual values. If, for example, an intervention or an operation on a patient is to be combined with an imaging procedure, the imaging procedure best suited for a particular patient can be employed as a function of the inventively determined causes of a deviation. If, for example, it is inventively identified that the preparation time for a morbid patient in a CT procedure is extended only by 5 minutes compared to an average preparation time, whereas an MR procedure requires a 15-minute-longer preparation time, in this case the intervention can be combined with a CT procedure, whereas in the case of a normal patient the intervention is combined with an MR procedure.

Because for example deviations and error patterns can be identified and dynamically monitored on the basis of time stamps, the workflow (i.e. the performance of the procedure) can be controlled interactively.

The present invention additionally has the following advantages:

An early person-independent identification of possible errors in the process (i.e. during the performance of the procedure).

A dynamic adjustment of the process.

Better scheduling of the process by a simulation, in which all parameters of the respective substep are captured.

The present invention enables new processes to be extended and adapted easily.

An increase in cost efficiency in the clinical workflow.

The inventively determined information (e.g. the cause of the deviation) can be employed for other processes (e.g. nursing, maintenance of the medical system).

The invention is suitable as a complete solution for a wide variety of clinic configurations and hospital systems and thus for centralized process control of multiple clinics or hospitals. Depending on the configuration only substeps or subareas can also be inventively monitored.

Because of the possibility of monitoring all workflow parameters of each substep or subprocess, optimization options exist that can ensure a considerable potential for savings.

The inventive archiving can be employed for documentation of substeps or process steps.

The inventively captured data can be analyzed for scheduling, billing or approaches to problems and can also for example be employed by a simulation for future products or planned chains of clinics.

BRIEF DESCRIPTION OF THE DRAWINGS

FIG. 4 is a flowchart of an embodiment of the inventive method.

DESCRIPTION OF THE PREFERRED EMBODIMENTS

Figure 1:
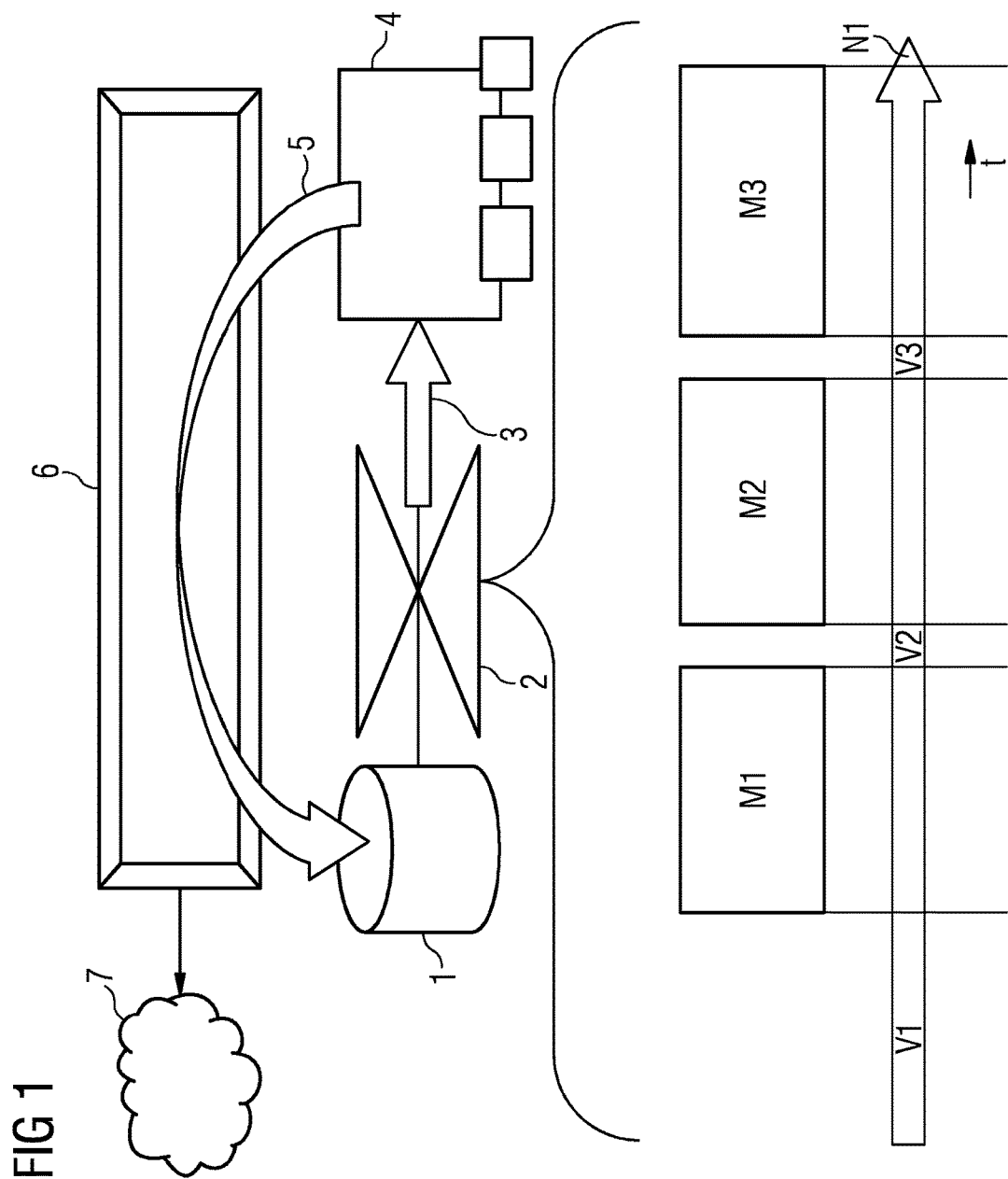
FIG. 1 is a schematic illustration of the inventive performance of a procedure.

FIG. 1 schematically illustrates the performance of a procedure on a patient by a medical system in accordance with the invention.

The procedure to be performed includes seven substeps:
three measurement steps M1-M3,
three preparation steps V1-V3 (one for each measurement step) and
an evaluation step N1 after the last measurement step M3.

For each of these substeps the actual time period, i.e. the duration over time of the respective substep, is automatically captured or measured. In a comparator 2 the actual time period is compared to a corresponding time period stored in a database 1 for each substep. If the comparator 2 determines a deviation 3 (in particular as a function of a threshold value) between the target time period and the actual time period, said deviation 3 is transferred to cause determination 4.

The cause determination 4 can be performed fully automatically, in order to determine a cause of the deviation 3 as a function of particular preconditions and parameters of the corresponding substep for which the deviation 3 was determined. It is however also possible for the cause determination 4 to take place at least partially manually. For said at least partially manual cause determination 4 the deviation can be provided as an output in a first step to a user who is executing the corresponding substep. The user (or another person) then has the option of confirming the present deviation 3 and (immediately or later) entering an input that indicates a cause of the deviation 3.

The deviation 3 and the determined cause can then be saved in the database 1 via a feedback loop 5. As a result the deviation and the cause can be employed, for example, to determine future target values (e.g. target time periods). In addition the deviation 3 and the cause can, for example, also be saved in other (interactive) databases 6 or in the cloud 7 via a web link (e.g. via the internet). As a result it is for example possible for the information on the deviation and the cause also to be provided to other medical systems, in order to improve corresponding substeps of said systems.

Figure 2:
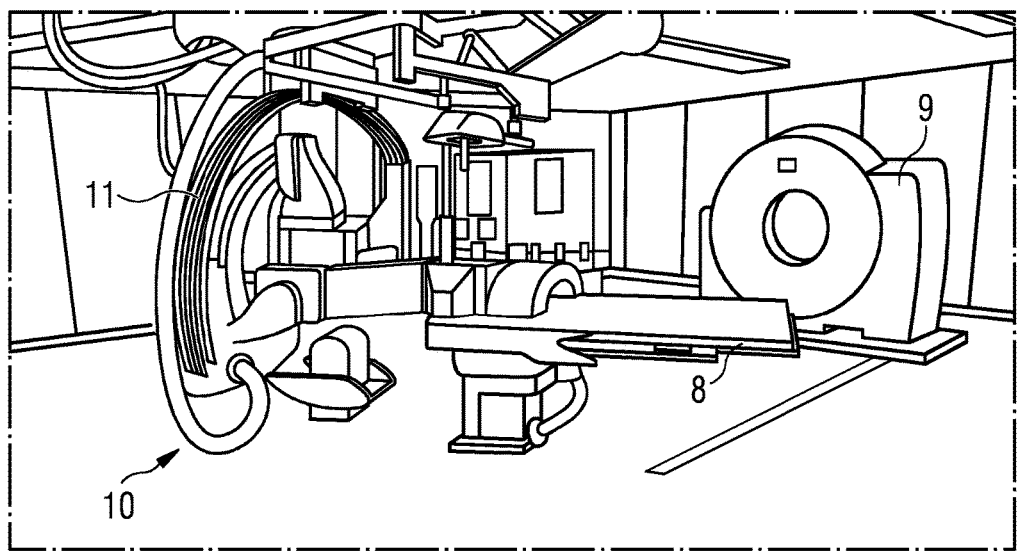
FIG. 2 shows an embodiment of the inventive medical system.

FIG. 2 shows an inventive medical system 10.

The medical system 10 shown enables both the performance of an examination and also the performance of an intervention on the same patient, without the patient having to be moved to another bed. To this end the patient is placed on the table 8 of the medical system 10. Lying on the table 8, either angiography can be performed using an angiography device 11 of the medical system 10, or image data of the patient can be captured using a CT system 9 of the medical system 10. In addition the patient who is lying on the table 8 can be operated on.

Figure 3:
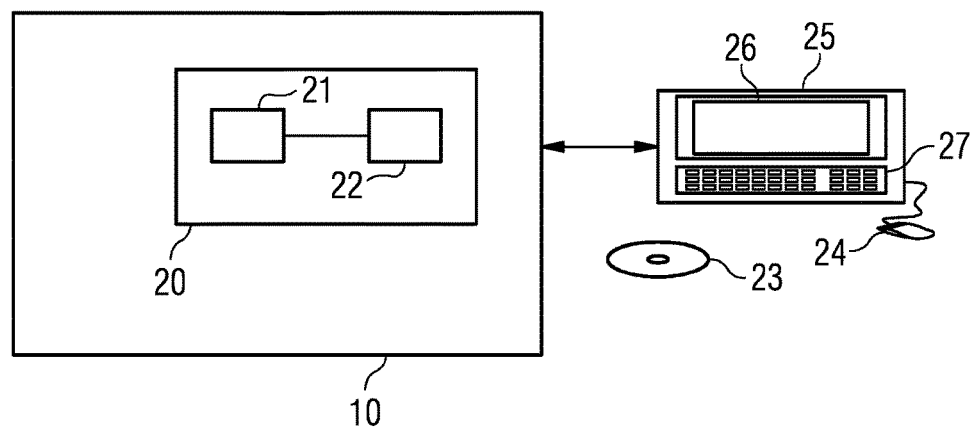
FIG. 3 is a schematic illustration of the inventive medical system.

FIG. 3 shows a schematic representation of an inventive medical system 10.

The medical system 10 shown in FIG. 3 has an inventive apparatus 20 which in turn includes a control computer 21 and sensor arrangement 22. In addition the medical system 10 has a terminal 25 which in turn has a monitor 26, a keyboard 27 and a mouse 24.

The inventive method can be implemented by instructions embodied in program code stored on a DVD 23.

A flowchart of the inventive method is shown in FIG. 4.

In a first step S1 target values (in particular target time periods) are determined for each substep of a procedure to be performed. This determination can take place by a simulation, by which the target values are determined as a function of parameters of the respective substep.

During the performance of the respective substep the actual values for the respective substep are automatically captured in step S2. If the actual values are time periods, a time stamp is generally captured automatically at the start and end of the respective substep, in order to calculate the actual time period of the respective time step as a function of said two time stamps.

In the following step S3 the target values and the actual values of the respective substep are compared, in order to determine a deviation for each substep. At least if this deviation exceeds a particular threshold value, the cause of the deviation is determined (automatically) in step S4. Depending on this cause, the performance of the substep and thus the performance of the procedure can then be improved in step S5. It is however also possible to optimize, based on the cause determined, the performance of other procedures which comprise a similar substep to the substep for which the deviation and the cause were determined.

Although modifications and changes may be suggested by those skilled in the art, it is the intention of the Applicant to embody within the patent warranted hereon all changes and modifications as reasonably and properly come within the scope of the Applicant's contribution to the art.

The invention claimed is:

1. A method for operating a medical system in order to perform a procedure on a patient, said procedure comprising a plurality of successively-performed steps, said method comprising:
   in a computer, determining target values for each of said steps of the procedure;
   during performance of said procedure, detecting actual values for each of said steps of the procedure and providing said actual values to said computer;
   in said computer, comparing the target values respectively to actual values for each of said steps of said procedure, in order to determine a deviation between each of the target values and each of the actual values, respectively; and
   in said computer, generating an electrical signal that represents said deviation between each target value and each actual value and providing said electrical signal representing the deviation as an output from said computer if an amount of said deviation is above a predetermined threshold value.

2. A method as claimed in claim 1 comprising, in said computer, automatically determining a cause of any deviation that exceeds said predetermined threshold value.

3. A method as claimed in claim 2 comprising:
operating said medical system to perform said procedure respectively on multiple patients; and
dependent on said cause of said deviation, controlling said medical system from said computer to change a sequence in which the procedure is respectively performed on a patient, in order to reduce said deviation.

4. A method as claimed in claim 3 comprising providing said output of said electrical signal from said computer prior to performing a respective step, for which said deviation exceeded said predetermined threshold, in order to prevent said deviation during a subsequent performance of that respective step in performance of said procedure on another patient.

5. A method as claimed in claim 1 wherein said steps are selected from the group consisting of preparation of a next step, evaluation of a previous step, a measurement in which measurement results are obtained from the patient by the medical system, and intervention on the patient using the medical system, and a treatment of the patient using the medical system.

6. A method as claimed in claim 1 wherein a target value for a respective step is a target time period that fixes a time duration in which that respective step is to be performed, and wherein an actual value for that respective step is an actual time period that fixes a time duration in which that respective step was performed.

7. A method as claimed in claim 1 comprising, in said computer, determining a target value for a respective step by simulating that respective step in said computer.

8. A method as claimed in claim 7 comprising, in said computer, if the deviation for that respective step exceeds said predetermined threshold value, determining, in said computer, a cause of said deviation, and executing said simulation dependent on the determined cause.

9. A method as claimed in claim 1 comprising, in said computer, optimizing said performance of said medical procedure by setting a positive deviation, in which the actual value is smaller than the corresponding target value.

10. An apparatus for controlling performance of a medical procedure, comprising a plurality of steps, by a medical system, said apparatus comprising:
a computer configured to determine target values for each of said steps of the procedure;
a sensor arrangement that detects, during performance of said procedure, actual values for each of said steps of the procedure and provides said actual values to said computer;
said computer being configured to compare the target values respectively to actual values for each of said steps of said procedure, in order to determine a deviation between each of the target values and each of the actual values, respectively; and
said computer being configured to generate an electrical signal that represents said deviation between each target value and each actual value and to provide said electrical signal representing the deviation as an output from said computer if an amount of said deviation is above a predetermined threshold value.

11. A medical system comprising:
a computer configured to determine target values for each of said steps of the procedure;
a sensor arrangement that detects, during performance of said procedure, actual values for each of said steps of the procedure and provides said actual values to said computer;
said computer being configured to compare the target values respectively to actual values for each of said steps of said procedure, in order to determine a deviation between each of the target values and each of the actual values, respectively; and
said computer being configured to generate an electrical signal that represents said deviation between each target value and each actual value and to provide said electrical signal representing the deviation as an output from said computer if an amount of said deviation is above a predetermined threshold value.

12. A medical system as claimed in claim 11 wherein said medical apparatus is an apparatus selected from the group consisting of a magnetic resonance apparatus, a computed tomography apparatus, an angiography apparatus, an x-ray apparatus, and an ultrasound apparatus.

13. A non-transitory, computer-readable data storage medium encoded with programming instructions, said storage medium being loaded into a computer system of a medical imaging system, and said programming instructions causing said computer system to:
determine target values for each of said steps of the procedure;
during performance of said procedure, receive detected actual values for each of said steps of the procedure and providing said actual values to said computer;
compare the target values respectively to actual values for each of said steps of said procedure, in order to determine a deviation between each of the target values and each of the actual values, respectively; and
generate an electrical signal that represents said deviation between each target value and each actual value and provide said electrical signal representing the deviation as an output from said computer if an amount of said deviation is above a predetermined threshold value.

* * * * *